US012582582B2

(12) United States Patent (10) Patent No.: US 12,582,582 B2
Mourao et al. (45) Date of Patent: Mar. 24, 2026

(54) ORAL CARE COMPOSITIONS AND METHODS OF USE

(71) Applicant: Colgate-Palmolive Company, New York, NY (US)

(72) Inventors: Marcella Mourao, Sao Paulo (BR); Enzo Utima, Sao Paulo (BR); Tatiana Cinquetti, Sao Paulo (BR)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 17/396,102

(22) Filed: Aug. 6, 2021

(65) Prior Publication Data

US 2022/0040064 A1 Feb. 10, 2022

Related U.S. Application Data

(60) Provisional application No. 63/061,950, filed on Aug. 6, 2020.

(51) Int. Cl.
| | |
|---|---|
| *A61K 8/19* | (2006.01) |
| *A61G 11/00* | (2006.01) |
| *A61K 8/34* | (2006.01) |
| *A61Q 11/00* | (2006.01) |

(52) U.S. Cl.
CPC .............. *A61K 8/19* (2013.01); *A61G 11/00* (2013.01); *A61K 8/34* (2013.01); *A61K 8/345* (2013.01)

(58) Field of Classification Search
CPC . A61K 8/19; A61K 8/34; A61K 8/345; A61Q 11/00
See application file for complete search history.

(56) References Cited

U.S. PATENT DOCUMENTS

| | | | |
|---|---|---|---|
| 8,758,785 B2 | 6/2014 | Miyamoto et al. | |
| 10,596,082 B2 * | 3/2020 | Utima .................... | A61Q 11/00 |

| | | | | |
|---|---|---|---|---|
| 2009/0214628 A1* | 8/2009 | de Rijk ...................... | C02F 1/50 | |
| | | | 424/47 | |
| 2011/0027328 A1* | 2/2011 | Baig .................... | A61K 8/8129 | |
| | | | 424/49 | |
| 2011/0293540 A1* | 12/2011 | Musa .................... | C08F 226/06 | |
| | | | 526/263 | |
| 2019/0359735 A1* | 11/2019 | Fischer ............... | C08B 37/0033 | |

FOREIGN PATENT DOCUMENTS

| | | | | |
|---|---|---|---|---|
| CA | 2980908 | 9/2016 | | |
| CN | 106667797 | 5/2017 | | |
| CN | 106667797 A * | 5/2017 | ............. | A61K 8/365 |
| WO | WO-2014056824 A2 * | 4/2014 | ........... | A61K 8/0241 |
| WO | 2014/088536 | 6/2014 | | |
| WO | 2018/156545 | 8/2018 | | |
| WO | WO-2018156545 A1 * | 8/2018 | ............. | A61Q 11/00 |

OTHER PUBLICATIONS

Makinen et al. Journal of Food Science, vol. 46, 1981, pp. 950-951 (Year: 1981).*
Umai et al. Frontiers in Sustainability, vol. 3, Feb. 2022, Article 826190, pp. 1-16 (Year: 2022).*
Anonymous, 2015, "Mint Toothpaste", Mintel Database GNPD AN: 3571295.
Anonymous, 2015, "Total Repair Organic Natural Toothpaste", Mintel Database GNPD AN: 3353933.
International Search Report and the Written Opinion of the International Searching Authority issued in International Application PCT/US2021/044978 mailed Nov. 29, 2021.
DaddyLab Your Health Care Guide, DaddyLab, Jiangsu Phoenix Literature and Art Publishing House, Oct. 2020, pp. 85-86.
Rongyiyitu et al., "Application of Food Preservatives," China Food Publishing House, Mar. 1987, p. 107.

* cited by examiner

*Primary Examiner* — Marianne C Seidel
*Assistant Examiner* — Amanda Michelle Petritsch

(57) ABSTRACT

Disclosed herein are improved oral care formulations comprising precipitated calcium carbonate (PCC) and synergistic preservative combinations selected. Methods of making and using the compositions are also provided.

11 Claims, No Drawings

ORAL CARE COMPOSITIONS AND METHODS OF USE

CROSS REFERENCE TO RELATED APPLICATIONS

This application claims the benefit of priority to U.S. Provisional Application No. 63/061,950, filed on Aug. 6, 2020, the contents of which are incorporated herein by reference in its entirety.

FIELD

This invention relates to improved oral care formulations comprising precipitated calcium carbonate (PCC) and a preservatives combination comprising pentylene glycol and/or caprylyl glycol and/or benzyl alcohol as well as to methods of using and of making these compositions.

BACKGROUND

Chalk and precipitated calcium carbonate (PCC) have the same composition—Calcite or calcium carbonate (CaCO3). However, the two are differentiated by their particle characteristics, e.g., particle morphology, purity, particle size and particle distribution, which is critical for use of calcium carbonate in toothpastes as cleaning/abrasive agent.

PCC is generally made from a high purity calcium carbonate rock called limestone, which has been subjected to high pressure over time and purified through diagenesis. If conditions are not optimal, limestone precursors (i.e., prehistoric organic materials) result in soft chalk.

PCC presents a number of advantages over ordinary chalk. Several points in the PCC process allows for the calcium carbonate purification, removing much of the rock from the deposit that is not calcium carbonate, such as feldspar, other silicaceous minerals, and heavy metals. Also, the PCC process allows to grow crystals of different shapes. The particle formed is dictated by the control of reaction time, temperature, agitation, pressure, rate of carbon dioxide addition, and post-crystallization processing. These shapes—clustered needles, cubes, prisms, rhombohedrons, scalenohedral—have different physical properties such as powder density, surface area and oil absorption, which give them outstanding performance in many applications where ground calcium carbonate does not perform as well.

Precipitated calcium carbonate (PCC) is manufactured on a commercial scale for use in a variety of industrial, cosmetic and pharmaceutical products. However, slurries of precipitated calcium carbonate, such as used in oral care compositions, are susceptible to microorganism contamination. To reduce the amount of viable microorganisms, a preservative, such as aldehyde, can be added to the slurry. For example, U.S. Patent Application Publication No. 2009/0088483 discloses combinations of a dialdehyde (such as glutaraldehyde) and a formaldehyde-releasing agent, such as (ethylenedioxy)dimethanol. Unfortunately, these preservatives have their limitations. Glutaraldehyde, for example, is unstable at alkaline pH, and is therefore ineffective as a long-term preservative for this kind of material. Furthermore, some bacterial strains metabolize formaldehyde (see, for example, Di Maiuta et al. (2009) International Biodeterioration & Biodegradation 63:769-777), permitting bacterial growth even in a treated PCC slurry.

Thus, there is a need for improved preservation ingredients for use in precipitated calcium carbonate containing compositions.

BRIEF SUMMARY

It has been surprisingly found that the inclusion of certain ingredient components within precipitated calcium carbonate containing oral care compositions may minimize microbial growth within the oral care composition. Minimization of microbial growth from an oral care product, such as a dentifrice formulation, may be useful for use in prolonging the shelf-life and ensuring the quality of oral care compositions.

In one embodiment, the present disclosure provides an oral care composition comprising precipitated calcium carbonate (PCC) and a preservative combination, comprising:
    a) pentylene glycol, and
    b) at least one of benzyl alcohol and caprylyl glycol.

In certain embodiments, the PCC in the oral care composition is present in an amount of 30-45% by weight of the composition. In further embodiments, PCC in the oral care composition is present in an amount of 30-45% by weight of the composition and pentylene glycol is present in an amount of about 0.1 wt. % to about 5.0 wt %, by total weight of the composition.

In certain embodiments, the invention is a method to improve oral health, oral hygiene, or oral appearance, comprising applying an effective amount of the oral care composition of any of the preceding embodiments set forth to the oral cavity of a subject in need thereof. In certain embodiments improving oral health may be selected from one or more of the following; a) reduce or inhibit formation of dental caries; b) reduce, repair or inhibit early enamel lesions; c) reduce or inhibit demineralization and promote remineralization of the teeth; d) reduce hypersensitivity of the teeth; e) reduce or inhibit gingivitis; f) promote healing of sores or cuts in the mouth; g) reduce levels of acid producing bacteria; h) to increase relative levels of arginolytic bacteria; i) inhibit microbial biofilm formation in the oral cavity; j) raise and/or maintain plaque pH at levels of at least pH 5.5 following sugar challenge; k) reduce plaque accumulation; l) treat, relieve or reduce dry mouth, m) whiten teeth; n) enhance systemic health, including cardiovascular health; o) reduce erosion of the teeth; p) immunize the teeth against cariogenic bacteria and their effects; q) clean the teeth and oral cavity; r) reduce inflammation; and s) increase anti-oxidant levels.

In certain embodiments, the invention is a composition obtained or obtainable by combining the ingredients as set forth in any of the preceding compositions and methods.

DETAILED DESCRIPTION

As used herein, the term "oral composition" means the total composition that is delivered to the oral surfaces. The composition is further defined as a product which, during the normal course of usage, is not, the purposes of systemic administration of particular therapeutic agents, intentionally swallowed but is rather retained in the oral cavity for a time sufficient to contact substantially all of the dental surfaces and/or oral tissues for the purposes of oral activity. Examples of such compositions include, but are not limited to, toothpaste or a dentifrice, a mouthwash or a mouth rinse, a topical oral gel, a denture cleanser, sprays, powders, strips, floss and the like.

As used herein, the term "dentifrice" means paste, gel, or liquid formulations unless otherwise specified. The dentifrice composition can be in any desired form such as deep striped, surface striped, multi-layered, having the gel surrounding the paste, or any combination thereof. Alternatively, the oral composition may be dual phase dispensed from a separated compartment dispenser.

Compositions of the Present Disclosure

In one aspect the invention is an oral care composition (Composition 1) An oral care composition comprising precipitated calcium carbonate (PCC) and a preservative combination, comprising:

a) pentylene glycol, and b) at least one of benzyl alcohol and caprylyl glycol.

For example, the invention contemplates any of the following compositions (unless otherwise indicated, values are given as percentage of the overall weight of the composition):

1.1 Composition 1, wherein the precipitated calcium carbonate is present in an amount of about 5 wt. % to about 75 wt. %, about 20 wt. % to about 55 wt. %, about 30 wt. % to about 45 wt. %, about 35 wt. % to about 40 wt. %, about 40 wt. % to about 45 wt. %, or about 42 wt. %, based on the total weight of the composition.

1.2 Any of the preceding compositions, wherein the preservative combination comprises or consists of pentylene glycol and benzyl alcohol.

1.3 Any of the preceding compositions, wherein the preservative combination comprises or consists of pentylene glycol and caprylyl glycol.

1.4 Any of the preceding compositions, wherein the preservative combination comprises or consists of pentylene glycol, benzyl alcohol and caprylyl glycol.

1.5 Any of the preceding compositions, wherein the composition comprises pentylene glycol in an amount of about 0.1 wt. % to about 5.0 wt %, about 0.5 wt. % to about 3.0 wt %, about 0.9 wt. % to about 2.0 wt. %, about 0.9 wt. %, about 1.0 wt. %, about 1.5 wt. % or about 2.0 wt. %, based on the weight of the composition.

1.6 Any of the preceding compositions, wherein the composition comprises caprylyl glycol in an amount of about 0.1 wt. % to about 1.0 wt %, about 0.2 wt. % to about 0.5 wt. %, about 0.2 wt. %, or about 0.5 wt. %, based on the weight of the composition.

1.7 Any of the preceding compositions, wherein the composition comprises benzyl alcohol in an amount of about 0.1 wt. % to about 1.0 wt %, or about 0.3 wt. %, based on the weight of the composition.

1.8 Any of the preceding compositions, further comprising an effective amount of a basic amino acid.

1.9 Any of the preceding compositions, further comprising a basic amino acid selected from arginine, glycine and lysine.

1.10 The preceding composition, wherein the basic amino acid is arginine in free or salt form.

1.11 The preceding composition, wherein the arginine is L-arginine.

1.12 Any of the preceding compositions, wherein the arginine is present in an amount corresponding to 0.1% to 10%, e.g., 0.1 wt. % to 3.0 wt. % of the total composition weight, about e.g., 0.5%, 1.0% 1.5%, 2.0%, 2.5%, or 3.0%, wherein the weight of the basic amino acid is calculated as free form.

1.13 Any of the preceding compositions, further comprising an abrasive or particulate selected from alumina, aluminum hydroxide, calcium carbonate, dicalcium phosphate, mica, sodium bicarbonate, calcium pyrophosphate or combinations thereof, wherein the abrasive or particulate is present in an amount of about 10 to 90 wt. %, about 20 to 70 wt. %, about 30 to 50 wt.

%, or about 35 to 45 wt. % (e.g., about 40%), calculated relative to the total weight of the composition.

1.14 Any of the preceding compositions, comprising silica wherein the silica is used as a thickening agent, e.g., particle silica.

1.15 Any of the preceding compositions, wherein the orally acceptable vehicle comprises one or more of water, a thickener, a buffer, a humectant, a surfactant, a sweetener, a pigment, a dye, an anti-caries agent, an anti-bacterial, a whitening agent, a desensitizing agent, a vitamin, a preservative, an enzyme, and mixtures thereof.

1.16 Any of the preceding compositions, wherein the composition comprises a humectant selected from glycerin, sorbitol, xylitol, propylene glycol or combinations thereof.

1.17 Any of the preceding compositions, comprising a humectant in an amount of 15 to 70 wt. % or 30 to 65 wt. %, based on the total weight of the composition.

1.18 Any of the preceding compositions wherein the pH of the composition is between 7.5 and 11.0, e.g., 8.0 and 10.2.

1.19 Any of the preceding compositions, wherein the pH of the composition is about 8.0, 9.0 or 10.0.

1.20 Any of the preceding compositions, further comprising a fluoride source selected from: sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

1.21 Any of the preceding compositions, wherein the composition comprises a fluoride source present in an amount of 0.01 wt. % to 2 wt. % (e.g., 0.1 wt %-1.0 wt. %) of the total composition weight.

1.22 Any of the preceding compositions, wherein the composition comprises more than one fluoride source.

1.23 Any of the preceding compositions, wherein the composition comprises a combination of sodium fluoride and sodium monofluorophosphate.

1.24 Any of the preceding compositions, wherein the composition comprises a combination of sodium fluoride present in an amount of about 0.01 to 0.2 wt %, based on the total weight of the composition, and sodium monofluorophosphate present in an amount of about 0.5 to 1.0 wt. %, based on the total weight of the composition.

1.25 Any of the preceding compositions wherein the fluoride source provides fluoride ion in an amount of from 50 to 25,000 ppm (e.g., 750-7000 ppm, e.g., 1000-5500 ppm, e.g., about 500 ppm, 1000 ppm, 1100 ppm, 2800 ppm, 5000 ppm, or 25000 ppm).

1.26 Any of the preceding compositions further comprising an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, disodium hydrogenorthophoshpate, monosodium phosphate, pentapotassium triphosphate and mixtures of any of two or more of these, e.g., in an amount of 0.01-20%, e.g., 0.1-8%, e.g., e.g., 0.1 to 5%, e.g., 0.3 to 2%, e.g., 0.3 to 1%, e.g. about 0.01%, about 0.1%, about 0.5%, about 1%, about 2%, about 5%, about 6%, by weight of the composition.

1.27 Any of the preceding compositions comprising tetrapotassium pyrophosphate, disodium hydrogenorthophoshpate, monosodium phosphate, and pentapotassium triphosphate.

1.28 Any of the preceding compositions comprising a polyphosphate.

1.29 The preceding composition, wherein the polyphosphate is tetrasodium pyrophosphate.

1.30 The preceding composition, wherein the tetrasodium pyrophosphate is from 0.01-1.0 wt % (e.g., about 0.25 wt %).

1.31 Any of the preceding compositions, further comprising an anionic surfactant, wherein the anionic surfactant is present in an amount of 0.1 wt. % to 5 wt. %, wherein the anionic surfactant is sodium lauryl sulfate and/or sodium laureth sulfate.

1.32 Any of the preceding compositions further comprising a nonionic surfactant, wherein the nonionic surfactant is in an amount of from 0.5-5%, selected from poloxamers (e.g., poloxamer 407), polysorbates (e.g., polysorbate 20), polyoxyl hydrogenated castor oil (e.g., polyoxyl 40 hydrogenated castor oil), and mixtures thereof.

1.33 The preceding composition, wherein the poloxamer nonionic surfactant has a polyoxypropylene molecular mass of from 3000 to 5000 g/mol and a polyoxyethylene content of from 60 to 80 mol %, e.g., the poloxamer nonionic surfactant comprises poloxamer 407.

1.34 Any of the preceding compositions further comprising sorbitol, wherein the sorbitol is in a total amount of 10-40% (e.g., about 23%).

1.35 Any of the preceding compositions, further comprising a zinc ion source selected from zinc oxide, zinc citrate, zinc lactate, zinc phosphate and combinations thereof.

1.36 The preceding composition, wherein the zinc ion source comprises or consists of a combination of zinc oxide and zinc citrate.

1.37 The preceding composition, wherein the ratio of the amount of zinc oxide (e.g., wt. %) to zinc citrate (e.g., wt %) is from 1.5:1 to 4.5:1 (e.g., 2:1, 2.5:1, 3:1, 3.5:1, or 4:1).

1.38 Either of the two preceding compositions, wherein the zinc citrate is in an amount of from 0.25 to 1.0 wt % (e.g., 0.5 wt. %) and zinc oxide may be present in an amount of from 0.75 to 1.25 wt % (e.g., 1.0 wt. %) based on the weight of the oral care composition.

1.39 Any of the preceding compositions, wherein the zinc ion source comprises zinc citrate in an amount of about 0.5 wt %.

1.40 Any of the preceding compositions, wherein the zinc ion source comprises zinc oxide in an amount of about 1.0 wt %.

1.41 Any of the preceding compositions, wherein the zinc ion source comprises zinc citrate in an amount of about 0.5 wt % and zinc oxide in an amount of about 1.0 wt %.

1.42 Any of the preceding compositions, further comprising a stannous ion source.

1.43 The preceding composition, wherein the stannous ion source is selected from stannous fluoride and stannous chloride.

1.44 The two preceding compositions, wherein the stannous is present in an amount of 1.45 Any of the preceding compositions further comprising an additional ingredient selected from: benzyl alcohol, Methylisothizolinone ("MIT"), Sodium bicarbonate, sodium methyl cocoyl taurate (tauranol), lauryl alcohol, and polyphosphate.

1.46 Any of the preceding compositions, wherein the composition further comprises a copolymer.

1.47 The preceding composition, wherein the copolymer is a PVM/MA copolymer.

1.48 The preceding composition, wherein the PVM/MA copolymer comprises a 1:4 to 4:1 copolymer of maleic anhydride or acid with a further polymerizable ethylenically unsaturated monomer; for example, 1:4 to 4:1, e.g. about 1:1.

1.49 The preceding composition, wherein the further polymerizable ethylenically unsaturated monomer comprises methyl vinyl ether (methoxyethylene).

1.50 Any of compositions 1.50-1.52, wherein the PVM/MA copolymer comprises a copolymer of methyl vinyl ether/maleic anhydride, wherein the anhydride is hydrolyzed following copolymerization to provide the corresponding acid.

1.51 Any of compositions 1.50-1.53, wherein the PVM/MA copolymer comprises a GANTREZ® polymer (e.g., GANTREZ® S-97 polymer).

1.52 Any of the preceding compositions, wherein the composition comprises a thickening agent selected from the group consisting of carboxyvinyl polymers, carrageenan, xanthan, hydroxyethyl cellulose and water soluble salts of cellulose ethers (e.g., sodium carboxymethyl cellulose and sodium carboxymethyl hydroxyethyl cellulose).

1.53 Any of the preceding compositions further comprising sodium carboxymethyl cellulose (e.g., from 0.5 wt. %-1.5 wt. %).

1.54 Any of the preceding compositions comprising from 5%-40%, e.g., 10%-35%, e.g., about 15%, 25%, 30%, and 35% water.

1.55 Any of the preceding compositions comprising an additional antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, honokiol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC), phenolic antiseptics, hexetidine, octenidine, sanguinarine, povidone iodine, delmopinol, salifluor, metal ions (e.g., copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.

1.56 Any of the preceding compositions comprising an antioxidant, e.g., selected from the group consisting of Co-enzyme Q10, PQQ, Vitamin C, Vitamin E, Vitamin A, BHT, anethole-dithiothione, and mixtures thereof.

1.57 Any of the preceding compositions comprising a whitening agent.

1.58 Any of the preceding compositions comprising a whitening agent selected from a whitening active selected from the group consisting of peroxides, metal chlorites, perborates, percarbonates, peroxyacids, hypochlorites, and combinations thereof.

1.59 Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example, calcium peroxyphosphate, sodium perborate, sodium carbonate peroxide, sodium peroxyphosphate, and potassium persulfate), or hydrogen peroxide polymer complexes such as hydrogen peroxide-polyvinyl pyrrolidone polymer complexes.

1.60 Any of the preceding compositions further comprising an agent that interferes with or prevents bacterial attachment, e.g. ethyl lauroyl arginiate (ELA) or chitosan.

1.61 Any of the preceding oral compositions, wherein the oral composition may be any of the following oral compositions selected from the group consisting of: a toothpaste or a dentifrice, a mouthwash or a mouth rinse, a topical oral gel, sprays, powders, strips, floss and a denture cleanser.

1.62 A composition obtained or obtainable by combining the ingredients as set forth in any of the preceding compositions.

In various embodiments, the present disclosure also provides for a composition obtained or obtainable by combining the ingredients as set forth in any of the preceding compositions.

The invention further comprises the use of a composition as set forth above in the manufacture of a Composition of the Invention, e.g., for use in any of the indications set forth in the above methods.

The following description of embodiment(s) of the invention is merely exemplary in nature and is in no way intended to limit the invention, its application, or uses.

All references cited herein are hereby incorporated by reference in their entireties. In the event of a conflict in a definition in the present disclosure and that of a cited reference, the present disclosure controls.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used throughout, ranges are used as shorthand for describing each and every value that is within the range. Any value within the range can be selected as the terminus of the range.

Unless stated otherwise, all percentages of composition components given in this specification are by weight based on a total composition or formulation weight of 100%. The term "wt %" is an abbreviation for weight percent. For example, "molecule A 40 wt %" is meant to exemplify a molecule A having 40% weight of a total composition or formulation of 100%. Further, molecule A 40 wt % will constitute 40 g of molecule A in a 100 g total composition of formulation.

As used herein, the term "oral composition" means the total composition that is delivered to the oral surfaces. The composition is further defined as a product which, during the normal course of usage, is not for the purposes of systemic administration of particular therapeutic agents, intentionally swallowed but is rather retained in the oral cavity for a time sufficient to contact substantially all of the dental surfaces and/or oral tissues for the purposes of oral activity. Examples of such compositions include, but are not limited to, a dentifrice, a mouthwash or a mouth rinse, a topical oral gel, a denture cleanser, dental strips, beads, varnish, toothpowder and the like.

As used herein, the term "dentifrice" means paste, powder, gel, or liquid formulations unless otherwise specified. In certain embodiments, the dentifrice is toothpaste. The dentifrice composition can be in any desired form such, as deep striped, surface striped, multi-layered, having the gel surrounding the paste, or any combination thereof. Alternatively, the oral composition may be dual phase dispensed from a separated compartment dispenser.

In preferred embodiments of this invention, the oral composition is a dentifrice. Such dentifrices may include toothpowder, a dental tablet, toothpaste (dental cream), or gel, or any other known form known to one of skill in the art.

The term "effective amount" as used herein means that the amount of the composition of the present invention is of sufficient quantity to achieve the intended purpose, such as, for example, to induce or cause teeth whitening in the subject.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

The oral care compositions of the present invention utilize precipitated calcium carbonate as an abrasive. The precipitated calcium carbonate particles are present in an amount of from 30 to 45 wt % based on the weight of the composition, further optionally from 35 to 40 wt % based on the weight of the composition. In certain embodiments, the calcium carbonate particles are present in an amount of from 40 to 45 wt % based on the weight of the composition. In further embodiments, the calcium carbonate particles are present in an amount of about 42 wt % based on the weight of the composition.

The present invention provides compositions comprising an orally acceptable carrier. As used herein, an "orally acceptable carrier" refers to a material or combination of materials that are safe for use in the compositions of the present invention, commensurate with a reasonable benefit/risk ratio. Preferably, the carrier does not substantially reduce the efficacy of the ingredients within the oral care composition, such as a peroxide complex or whitening agent. Selection of specific carrier components is dependent on the desired product form, including dentifrices, rinses, gels, and paints. In various embodiments, the carrier is operable to sufficiently adhere the peroxide complex against surfaces within the oral cavity to which the composition is administered, without concomitant use of a dental tray, mouthpiece, tape, or similar appliance. In various embodiments, the carrier is operable for use with a tape, tray, mouthpiece or similar appliance.

Materials among those that are useful in carriers include adhesion agents, viscosity modifiers, diluents, surfactants, foam modulators, peroxide activators, peroxide stability agents, abrasives, pH modifying agents, humectants, mouth feel agents, sweeteners, flavorants, colorants, and combinations thereof. It is understood that while general attributes of each of the above categories of materials may differ, there may be some common attributes and any given material may serve multiple purposes within two or more of such categories of materials. Preferably, such carrier materials are selected for compatibility with the peroxide complex and with other ingredients of the composition.

In various preferred embodiments, the orally acceptable carrier may comprise polymers and/or copolymers of polyethylene glycol, of ethylene oxide propylene oxide, and of silicone. If such copolymers/polymers are used, they may be selected from the commercially available materials PLURAFLO® L4370 and PLURAFLO® L1220 (available from BASF, Wyandotte, Mich., United States of America). In one embodiment such polymer and/or copolymer is an ethylene oxide, propylene oxide block co-polymer of formula (ethylene oxide)x-(propylene oxide)y wherein x is an integer of 80-150, e.g. 100-130, e.g. about 118, and y is an integer 30-80, e.g. about 60-70, e.g. about 66, having an average molecular weight of greater than 5000, e.g., 8000-13000 Da, e.g. about 9800. Block copolymers of ethylene oxide/propylene oxide are useful, but higher molecular weight, e.g., >5000 Da are preferred, e.g. including PLURACARE® L1220 (available from BASE, Wyandotte, Mich., United States of America). Low or medium molecular weight polyethylene glycol, e.g., PEG 400, PEG 600, PEG 800, PEG 1000 and mixtures thereof are also useful. It is preferred that the carrier(s) provide a dentifrice with a viscosity of about 10,000 CPS to about 700,000 CPS, preferably about 30,000 CPS to about 300,000 CPS.

The toothpaste compositions may further comprise, in addition to the precipitated calcium carbonate particles, one or more further abrasive particulates. Any abrasive particulates may be used and may be selected from sodium bicarbonate, calcium phosphate (e.g., dicalcium phosphate dihydrate), calcium pyrophosphate calcium sulfate, silica, iron oxide, aluminium oxide, perlite, plastic particles, e.g., polyethylene, and combinations thereof. Any type of silica may be used, such as hydrated silica, precipitated silica or silica gel. Optionally, the oral care composition further comprises, as a thickener and also as an abrasive, silica particles in an amount of from 1 to 3 wt % based on the weight of the composition.

Certain abrasives may be used which portray dual functionality. In one embodiment, the toothpaste composition comprises silica that has a particle size and an amount and distribution in the toothpaste composition so that the silica has a dual function, and functions not only as a dentin tubule-occluding particulate but also as an abrasive particulate. Such a dual function particulate may be provided by a commercially available silica such as INEOS AC43 (Ineos Silicas, Warrington, United Kingdom). In an embodiment, such silica has a median particle size less than 8 μm, for example from 3 μm to 5 μm.

The compositions of the present invention may further comprise an abrasive useful for example as a polishing agent. Any orally acceptable abrasive can be used, but type, fineness, (particle size) and amount of abrasive should be selected so that tooth enamel is not excessively abraded in normal use of the composition. Suitable abrasives include silica, for example in the form of precipitated silica or as admixed with alumina, insoluble phosphates, and mixtures thereof. Among insoluble phosphates useful as abrasives are orthophosphates, polymetaphosphates and pyrophosphates. Illustrative examples are dicalcium orthophosphate dihydrate, calcium pyrophosphate, calcium pyrophosphate, tricalcium phosphate, calcium polymetaphosphate and insoluble sodium polymetaphosphate.

In an embodiment, the abrasive particles may be initially present in the oral care composition, for example, a toothpaste, having the desired particle size, or may be initially present in the composition at a larger size, so long as the structure of the particles is such that it fractures or breaks into the desired particle size upon application of mechanical force by, e.g., a toothbrush, when brushing. In some embodiments, the dentifrice contains one or more humectants.

In some embodiments, the present invention further provides oral care compositions comprising: a cross-linked polyvinylpyrrolidone complexed with hydrogen peroxide, a stabilizing amount of an additional linear and/or cross-linked polyvinylpyrrolidone, precipitated calcium carbonate (PCC) and preservatives selected from the group consisting of i) phenethyl alcohol and caprylyl glycol, and ii) benzyl alcohol and caprylyl glycol.

The invention may contain whitening agents. Some embodiments provide non-aqueous dentifrice compositions comprising from 5 to 20 wt % cross-linked polyvinylpyrrolidone complexed with hydrogen peroxide (PVP—H$_2$O$_2$). Other embodiments provide oral care compositions comprising from 5 to 12 wt % cross-linked polyvinylpyrrolidone complexed with hydrogen peroxide. Still other embodiments provide oral care compositions comprising from 9 to 12 wt % cross-linked polyvinylpyrrolidone complexed with hydrogen peroxide. Yet other embodiments provide non-aqueous dentifrice compositions comprising 11 wt % cross-linked polyvinylpyrrolidone complexed with hydrogen peroxide.

In some embodiments, the present invention provides non-aqueous dentifrice compositions comprising from 0.03 to about 3 wt % of an additional linear and/or crosslinked polyvinylpyrrolidone. Some embodiments provide compositions comprising 1.75 wt %, by weight, of an additional linear and/or cross-linked polyvinylpyrrolidone.

The invention may contain additional whitening agents in addition to PVP—H$_2$O$_2$. Any whitening agent known or developed in the art may be used. Preferably, the whitening agent includes solid whitening agents and bound whitening agents which are substantially anhydrous oxygen generating compounds. Solid whitening agents useful herein include peroxides, metal chlorites, persulfate. Exemplary peroxide phases include hydroperoxides, hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include urea peroxide, glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as and perborate salts of alkali and alkaline earth metals such as lithium, potassium, sodium, magnesium, calcium and barium, and mixtures thereof. Preferred solid peroxides are sodium perborate, urea peroxide, and mixtures thereof. Suitable metal chlorites include calcium chlorite, barium chlorite, magnesium chlorite, lithium chlorite, sodium chlorite, and potassium chlorite. The whitening agent may be preferably bound. For example, peroxide may be bound to a polymer such as PVP (poly(N-vinylpyrrolidone)). Suitable PVP complexes are disclosed, for example, in U.S. Pat. No. 5,122,370, the contents of which are incorporated herein by reference. In some embodiments, it may be desirable to use any known whitening agent except sodium percarbonate and/or any of the percarbonate salts.

In various preferred embodiments, the non-aqueous dentifrice comprises a substantially anhydrous orally acceptable carrier and various dentifrice ingredients to adjust the rheology and feel of the composition such as humectants, surface active agents, thickening or gelling agents, etc.

Flavorants, sweeteners, colorants, foam modulators, mouth-feel agents and others additively may be included if desired, in the composition.

The oral care composition can optionally include at least one orally acceptable source of fluoride ions. Any known or to be developed in the art may be used. Suitable sources of fluoride ions include fluoride, monofluorophosphate and fluorosilicate salts. One or more fluoride ion-releasing compound is optionally present in an amount providing a total of about 100 to about 20,000 ppm, about 200 to about 5,000 ppm, or about 500 to about 2,500 ppm, fluoride ions.

The compositions of the present invention optionally comprise an antimicrobial (e.g., antibacterial) agent. A further illustrative list of useful antibacterial agents is provided in such as those listed in U.S. Pat. No. 5,776,435 to Gaffar et al., the contents of which are incorporated herein by reference. One or more antimicrobial agents are optionally present in an antimicrobial effective total amount, typically about 0.05% to about 10%, for example about 0.10% to about 3%.

The compositions of the present invention optionally comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

The compositions of the present invention optionally comprise a sialagogue or saliva-stimulating agent, an antiplaque agent, an anti-inflammatory agent, a desensitizing.

In various embodiments of the present invention, the oral composition comprises an anticalculus (tartar control) agent. Generally, tartar control agents are categorized as being incompatible with some whitening agents, but embodiments of the present invention incorporate tartar control agents and whitening agents in a single phase whitening composition. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. In some embodiments the anticalculus agent is present at about 0.1% to about 30%. The oral composition may include a mixture of different anticalculus agents. In one preferred embodiment, tetrasodium pyrophosphate (TSPP) and/or sodium acid pyrophosphate (SAPP) are used. In the one embodiment, the anticalculus agent comprises TSPP at about 1-2% and SAPP at about 0.5 to 5%. In a second preferred embodiment, tetrasodium pyrophosphate (TSPP) and/or sodium tripolyphosphate (STPP) are used. In the second preferred embodiment, the anticalculus agent comprises TSPP at about 1-2% and STPP at about 7% to 10%.

The compositions of the present invention optionally comprise a thickener. Any orally acceptable thickening agent can be used, including without limitation carbomers, also known as carboxyvinyl polymers, carrageenans, also known as Irish moss and more particularly-carrageenan (iota-carrageenan), high molecular weight polyethylene glycols (such as CARBOWAX®, available from The Dow Chemical Company), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, and colloidal and/or fumed silica and mixtures of the same. One or more thickening agents are optionally present in a total amount of about 0.1% to about 90%, for example about 1% to about 50% or about 5% to about 35%.

Thickening agents suitable for use in the compositions of the present invention include natural and synthetic gums and colloids. Suitable thickening agents include naturally occurring polymers such as carrageenan, xanthan gum, polyglycols of varying molecular weights sold under the tradename Polyox, and polyvinylpyrrolidone. Compatible inorganic thickening agents include amorphous silica compounds which function as thickening agents and include colloidal silicas compounds available under the trade designation Cab-o-sil (Cabot Corporation and distributed by Lenape Chemical, Bound Brook, N.J.), Zeodent 165 (J. M. Huber Chemicals Division, Havre de Grace, Md.); and Sylodent 15 (Davison Chemical Division of W. R. Grace Corporation, Baltimore, Md.). Other inorganic thickening agents include natural and synthetic clays such as hectorite clays, lithium magnesium silicate (laponite) and magnesium aluminum silicate (Veegum). In certain embodiments, the thickening agent may be selected from carrageenan (Iris moss), xanthan gum, starch, polyvinyl pyrrolidone and amorphous silicas, or any combination thereof.

While ingredients are sometimes identified herein by category, e.g., humectant, antioxidant, thickener, etc., this identification is for convenience and clarity, but is not intended to be limiting. All of the ingredients in the compositions may have functions in addition to their primary function, and may contribute to the overall properties of the composition, including its stability, efficacy, consistency, mouth feel, taste, odor and so forth.

In some embodiments, the sweetener may be sodium saccharin.

In certain embodiments, the buffering agents may be a sodium phosphate buffer (e.g., sodium phosphate monobasic and disodium phosphate).

Surfactants may be included, if desired. Examples of suitable surfactants include water-soluble salts of higher fatty acid monoglyceride monosulfates, such as the sodium salt of monosulfated monoglyceride of hydrogenated coconut oil fatty acids; higher alkyl sulfates such as sodium lauryl sulfate; alkyl aryl sulfonates such as sodium dodecyl benzene sulfonate; higher alkyl sulfoacetates, such as sodium lauryl sulfoacetate; higher fatty acid esters of 1,2-dihydroxypropane sulfonate; and the substantially saturated higher aliphatic acyl amides of lower aliphatic amino carboxylic compounds, such as those having 12-16 carbons in the fatty acid, alkyl or acyl radicals; and the like. Examples of the last mentioned amides include N-lauryl sarcosine, and the sodium, potassium and ethanolamine salts of N-lauryl, N-myristoyl, or N-palmitoyl sarcosine. Others include, for example, nonanionic polyoxyethylene surfactants, such as Polyoxamer 407, Steareth 30, Polysorbate 20, and castor oil; and amphoteric surfactants, such as cocamidopropyl betaine (tegobaine), and cocamidopropyl betaine lauryl glucoside; condensation products of ethylene oxide with various hydrogen containing compounds that are reactive therewith and have long hydrocarbon chains (e.g., aliphatic chains of from 12 to 20 carbon atoms), which condensation products (ethoxamers) contain hydrophilic polyoxyethylene moieties, such as condensation products of poly (ethylene oxide) with fatty acids, fatty, alcohols, fatty amides and other fatty moieties, and with propylene oxide and polypropylene oxides. In some embodiments, the surfactant may be sodium lauryl sulfate (SLS). In further embodiments, suitable surfactants include, without limitation, water-soluble salts of ethylene-20 alkyl sulfates, sulfonated monoglycerides of C8-20 fatty acids, sarcosinates, taurates, sodium lauryl sulfate, sodium coroyl monoglyceride sulfonate, sodium lauryl sarcosinate, sodium lauryl isoethionate, sodium laureth carboxylate and sodium dodecyl benzenesulfonate, and cocoamidopropyl betaine.

The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent is incorporated in the oral composition at a concentration of 0.1 to about 5% by weight. In certain embodiments, the flavoring agent is incorporated at 0.5 to 2.0% by weight.

pH modifying agents among those useful herein include acidifying agents to lower pH, basifying agents to raise pH, and buffering agents to control pH within a desired range. For example, one or more compounds selected from acidifying, basifying and buffering agents can be included to provide a pH of 2 to 10, or in various embodiments from 2 to 8, from 3 to 9, from 4 to 8, from 5 to 7, from 6 to 10, and from 7 to 9. Any orally acceptable pH modifying agent can be used, including without limitation carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and mixtures thereof. One or more pH modifying agents are optionally present in a total amount effective to maintain the composition in an orally acceptable pH range.

In certain aspects, methods are provided to improve oral health by applying an effective amount of any of the oral care composition described herein to the oral cavity of a subject in need thereof. In certain embodiments, the methods utilize an oral care composition comprising precipitated calcium carbonate (PCC), phenethyl alcohol and caprylyl glycol. In further embodiments, the PCC in the oral care composition is present in an amount of 30-45% by weight of the composition. In further embodiments, PCC in the oral care composition is present in an amount of 30-45% by weight of the composition and phenethyl alcohol is present in an amount of 0.1 to 1.0% by weight of the composition. In further embodiments, PCC in the oral care composition is present in an amount of 30-45% by weight of the composition, phenethyl alcohol is present in an amount of 0.1 to 1.0% by weight of the composition and caprylyl glycol is present in an amount of 0.1 to 1.0% by weight of the composition. In yet further embodiments, phenethyl alcohol is present in an amount of 0.2 to 0.3% by weight of the composition and caprylyl glycol is present in an amount of 0.13 to 0.2% by weight of the composition.

In certain embodiments, the methods utilize an oral care composition comprising PCC, pentylene glycol, benzyl alcohol and caprylyl glycol. In further embodiments, the PCC is present in an amount of 30-45% by weight of the composition. In further embodiments, PCC in the oral care composition is present in an amount of 30-45% by weight of the composition and benzyl alcohol is present in an amount of 0.1 to 1.0% by weight of the composition. In further embodiments, PCC in the oral care composition is present in an amount of 30-45% by weight of the composition, benzyl alcohol is present in an amount of 0.1 to 1.0% by weight of the composition and caprylyl glycol is present in an amount of 0.1 to 1.0% by weight of the composition. In further embodiments, benzyl alcohol is present in an amount of 0.2 to 0.3% by weight of the composition and caprylyl glycol is present in an amount of 0.13 to 0.2% by weight of the composition.

In certain embodiments, the improvement in oral health may be selected from one or more of the following; a. reduce or inhibit formation of dental caries; b. reduce, repair or inhibit early enamel lesions; c. reduce or inhibit demineralization and promote remineralization of the teeth; d. reduce hypersensitivity of the teeth; e. reduce or inhibit gingivitis; f. promote healing of sores or cuts in the mouth; g. reduce levels of acid producing bacteria; h. to increase relative levels of arginolytic bacteria; i. inhibit microbial biofilm formation in the oral cavity; j. raise and/or maintain plaque pH at levels of at least pH 5.5 following sugar challenge; k. reduce plaque accumulation; l. treat, relieve or reduce dry mouth; m. whiten teeth; n. enhance systemic health, including cardiovascular health; o. reduce erosion of the teeth; p. immunize the teeth against cariogenic bacteria and their effects; q. clean the teeth and oral cavity; r. reduce inflammation; and s. increase anti-oxidant levels.

In one embodiment, the composition remains stable when stored for at least 1 week, at least 2 weeks, at least 1 month, at least 3 months, at least 6 months, or at least 1 year. In one embodiment, the composition is stored at room temperature.

In further embodiments, methods are provided to improve oral health of a human or animal subject comprising contacting any composition described herein with the oral surface of the human or animal subject. As used herein "animal subject" includes higher order non-human mammals such as canines, felines, and horses. The oral care composition is contacted with an oral surface of the mammalian subject to thereby improve oral health in a highly efficacious manner.

In various embodiments, it is preferred that the oral care composition is applied and contacted with the oral surface. The dentifrice, prepared in accordance with the present invention is preferably applied regularly to an oral surface, preferably on a daily basis, at least one time daily for multiple days, but alternately every second or third day. Preferably the oral composition is applied to the oral surfaces from 1 to 3 times daily, for at least 2 weeks up to 8 weeks, from four months to three years, or more up to lifetime.

The compositions of the invention can be packaged into containers or dispensers known in the art, via means conventional in the art. In some embodiments the compositions are packaged into tubes, metal, plastic or laminated, with either screw top or flip top caps.

Example 1—Antibacterial Effect of Preservative Combinations Selected from Pentylene Glycol, Benzyl Alcohol and Caprylyl Glycol Various test compositions were created to screen for ingredients that could improve the antibacterial micro-robustness of PCC-based formulas. Tests were conducted using the widely used preservative benzyl alcohol at 0.3 wt. %. Further PCC-based compositions were created containing caprylyl glycol alone, pentylene glycol alone, as well as the combination of both caprylyl glycol and pentylene glycol.

All test formulations shared a common PCC base (Table 1), but varied the concentrations of caprylyl glycol (i.e., from 0.0 wt. % to 0.5 wt. %), pentylene glycol (i.e., from 0.0 wt. % to 1.0 wt. %), and benzyl alcohol (i.e., from 0.0 wt. % to 0.3 wt. %) and the combinations between them. Test compositions used are summarized in Table 2 below.

TABLE 1

PCC base formulation

| Ingredient | Quantity Range (%) |
|---|---|
| Glycerin | 10-20 |
| Water | 30-40 |
| Carboxymethyl cellulose | 0.1-1.0 |
| Sodium Saccharin | 0.1-0.5 |
| Sodium Monofluorophosphate | 0.5-2.0 |
| Sodium hydroxide | 0.05-1.0 |
| Tetrasodium Pyrophosphate | 0.1-1.0 |
| Precipitated Calcium Carbonate | 35-45 |
| Sodium Bicarbonate | 0.1-1.0 |
| Sodium Lauryl Sulfate | 0.5-2.0 |
| Caprylyl Glycol | 0.0-0.7 |
| Pentylene Glycol | 0.0-1.5 |
| Benzyl Alcohol | 0.0-0.4 |

TABLE 2

Test composition formulations

| Test Composition | Benzyl Alcohol (wt. %) | Caprylyl Glycol (wt. %) | Pentylene Glycol (wt. %) |
|---|---|---|---|
| 1 | 0.3 | 0.5 | 1.0 |
| 2 | 0.3 | 0.0 | 1.0 |
| 3 | 0.3 | 0.5 | 0.0 |
| 4 | 0.3 | 0.0 | 0.0 |
| 5 | 0.0 | 0.5 | 0.0 |
| 6 | 0.0 | 0.5 | 1.0 |
| 7 | 0.0 | 0.0 | 1.0 |
| 8 | 0.0 | 0.0 | 0.0 |

A first antibacterial assay was prepared to test the antibacterial efficacy of the Bacterial counts were taken at established points after exposing cultures to the test formulations: 4 hours, 6 hours and 24 hours, summarized in Table 2. In order to assess the microrobustness index (MRI) of a composition, a sample of the composition may be challenged with a certain quantity of various bacteria. For example, in certain embodiments, a sample formulation may be exposed to microorganisms including *Burkholderia cepacian, Enterobacter cloacae, Escherichia coli, Klebsiella oxytoca, Klebsiella pneumoniae, Serratia marcescens, Providencia rettgeri, Pseudomonas aeruginosa, Pseudomonas putida, Staphylococcus aureus*, and *Staphylococcus saprophyticus.*

The micro-robustness index is a quantitative measure of the sample's ability to resist microbial insult calculated from the area under the curve (AUC), in a plot of bacterial count against time. The composition under test was diluted in culture media and then added to inoculum to form the test material. At selected time intervals, the test material and the control (i.e., inoculum with no test composition present) were sampled. Dilutions and plating were performed to recover the surviving organisms, and bacterial counts (in terms of colony forming units, CFU) were carried out for both the test material and the control. The log difference in the bacterial counts between the test material and the inoculum control was calculated at these different time intervals.

TABLE 3

STD bacterial pool assay

| Test Composition | Microrobustness Index (MRI) | Log Reduction 4 h | Log Reduction 6 h | Log Reduction 24 h |
|---|---|---|---|---|
| 1 | 1.0 | 6.8 | 6.8 | 6.8 |
| 2 | 0.90 | 5.2 | 6.0 | 6.8 |
| 3 | 0.91 | 5.5 | 5.9 | 6.8 |
| 4 | 0.82 | 3.8 | 5.0 | 6.8 |
| 5 | 0.77 | 4.3 | 4.1 | 6.8 |
| 6 | 0.97 | 5.5 | — | 6.8 |
| 7 | 0.68 | 2.5 | 3.4 | 6.8 |
| 8 | 0.09 | 0.5 | 1.2 | 0.0 |

A second antibacterial assay was prepared to test the antibacterial efficacy of the Bacterial counts were taken at established points after exposing cultures to the test formulations: 4 hours, 24 hours and 120 hours, summarized in Table 2. In order to assess the microrobustness index (MRI) of a composition, a sample of the composition may be challenged with a certain quantity of various bacteria. For example, in certain embodiments, a sample formulation may be exposed to microorganisms including several types of *Halomonas* bacteria.

TABLE 4

Halomonas bacterial pool assay

| Test Composition | Log Reduction 4 h | Log Reduction 24 h | Log Reduction 120 h |
|---|---|---|---|
| 1 | 5.4 | 6.1 | 6.1 |
| 2 | 4.8 | 6.1 | 6.1 |
| 3 | 5.0 | 6.1 | 6.1 |
| 4 | 4.0 | 6.1 | 6.1 |
| 5 | 2.7 | 3.0 | 6.1 |
| 6 | 3.3 | 5.8 | 5.8 |
| 7 | 1.5 | 6.1 | 6.1 |
| 8 | 1.0 | 6.1 | 0.0 |

As shown, when caprylyl glycol is added to a composition containing both pentylene glycol and benzyl alcohol, the results show fast micro bioburden reduction at 4 hours versus the other Test Compositions (See Test Composition 1). Both pentylene glycol and benzyl alcohol, when used alone, only fully reduced bioburden after a period of 24 hours. When analyzing the combination of pentylene glycol and caprylyl glycol, a superior bioburden reduction is observed at 4 h versus caprylyl glycol alone as well as benzyl alcohol alone. These results suggest that caprylyl glycol has synergy with pentylene glycol and benzyl alcohol by showing faster micro bioburden reduction versus caprylyl glycol alone and pentylene glycol alone.

Example 2—Antibacterial Effect of Caprylyl
Glycol in Combination with Pentylene Glycol Test compositions were created similarly to those of
Example 1, but with combinations of varying concentrations
of pentylene glycol and caprylyl glycol. The Test Compositions created are listed in Table 4. Using a more challenging toothpaste base (Table 5), PCC backbone, no SLS, natural derived ingredients, a new round of tests was performed increasing pentylene glycol concentration to 1.5% and 2.0% based on previous results and applying an optimum level of 0.2% caprylyl glycol and 0.9% pentylene glycol in synergy vs a placebo with no preservatives. All 3 samples presented full bioburden reduction at 24 h and the placebo did not achieve this reduction.

TABLE 5

| Challenging toothpaste base | |
| --- | --- |
| Ingredient | Quantity Range (%) |
| Glycerin | 35-45 |
| Water | 10-20 |
| Carboxymethyl cellulose | 0.1-1.0 |
| Precipitated Calcium Carbonate | 35-45 |
| Cocamidopropyl Betaine | 1.5-4.5 |
| Sodium Monofluorophosphate | 0.5-2.0 |
| Xylitol | 2.0-6.0 |
| Stevia | 0.05-0.5 |
| Caprylyl Glycol | 0.0-0.2 |
| Pentylene Glycol | 0.0-2.0 |

TABLE 6

| Test composition formulations | | |
| --- | --- | --- |
| Test Composition | Caprylyl Glycol (wt. %) | Pentylene Glycol (wt. %) |
| 9 | 0.0 | 0.0 |
| 10 | 0.0 | 1.5 |
| 11 | 0.0 | 2.0 |
| 12 | 0.2 | 0.9 |

A first antibacterial assay was prepared to test the antibacterial efficacy of the Bacterial counts were taken at established points after exposing cultures to the test formulations: 4 hours, 6 hours and 24 hours, summarized in Table 5.

TABLE 7

| STD bacterial pool assay | | | | |
| --- | --- | --- | --- | --- |
| Test Composition | Microrobustness Index (MRI) | Log Reduction 4 h | Log Reduction 6 h | Log Reduction 24 h |
| 9 | 0.31 | 2.2 | 1.5 | 2.8 |
| 10 | 0.57 | 2.2 | 2.5 | 6.0 |
| 11 | 0.63 | 2.2 | 2.6 | 6.8 |
| 12 | 0.59 | 2.0 | 2.1 | 6.8 |

A second antibacterial assay was prepared to test the antibacterial efficacy of the Bacterial counts were taken at established points after exposing cultures to the test formulations: 4 hours, 24 hours and 120 hours, summarized in Table 2.

TABLE 8

| Halomonas bacterial pool assay | | | |
| --- | --- | --- | --- |
| Test Composition | Log Reduction 4 h | Log Reduction 24 h | Log Reduction 120 h |
| 9 | 2.7 | 2.7 | 5.2 |
| 10 | 5.2 | 5.2 | 5.2 |
| 11 | 5.2 | 5.2 | 5.2 |
| 12 | 5.2 | 5.2 | 5.2 |

Thus, the combination of pentylene glycol from up to 2.0 wt. % and its synergy with caprylyl glycol up to 0.5 wt. % show bioburden reduction efficacy on PCC based toothpaste formulations.

The invention claimed is:

1. An oral care composition comprising:
   precipitated calcium carbonate (PCC);
   pentylene glycol in an amount of about 0.1 wt. % to about 5.0 wt. %, based on the weight of the composition;
   caprylyl glycol in an amount of about 0.1% to about 1.0%, based on the weight of the composition;
   benzyl alcohol in an amount of about 0.1% to about 1.0%, based on the weight of the composition; and
   optionally, xylitol
   wherein the composition achieves a log reduction in microbial bioburden of greater than 5.0 after 4 hours when challenged with *Halomonas* bacterial pool assay in a PCC base comprising a surfactant.

2. The oral care composition according to claim 1, wherein the precipitated calcium carbonate is present in an amount of 5 wt. % to about 75 wt. %, based on the total weight of the composition.

3. The oral care composition according to claim 1, wherein the pentylene glycol is present in an amount of about 0.5 wt. % to about 3.0 wt. %, based on the weight of the composition.

4. The oral care composition according to claim 1, wherein the composition comprises caprylyl glycol in an amount of about 0.1 wt. % to about 0.5 wt. %, about 0.2 wt. % to about 0.5 wt. %, about 0.2 wt. %, or about 0.5 wt. %, based on the weight of the composition.

5. The oral care composition according to claim 1, further comprising a humectant present in an amount of 10.0 to 30.0% by weight of the composition.

6. The oral care composition according to claim 1, further comprising a surfactant present in an amount of 1.0 to 6.0% by weight of the composition.

7. The oral care composition according to claim 1, further comprising a flavor present in an amount of 0.5 to 2.0% by weight of the composition.

8. A method to improve oral health, oral hygiene, or oral appearance comprising applying an effective amount of the oral care composition according to claim 1 set forth above to the oral cavity of a subject in need thereof.

9. The oral care composition according to claim 1, wherein the composition is a dentifrice.

10. The method of claim 8, wherein improving oral health may be selected from one or more of the following,
   a. reduce or inhibit formation of dental caries:
   b. reduce, repair or inhibit early enamel lesions;
   c. reduce or inhibit demineralization and promote remineralization of the teeth;
   d. reduce hypersensitivity of the teeth;
   e. reduce or inhibit gingivitis;
   f. promote healing of sores or cuts in the mouth;
   g. reduce levels of acid producing bacteria;

h. to increase relative levels of arginolytic bacteria;

i. inhibit microbial biofilm formation in the oral cavity;

j. raise and/or maintain plaque pH at levels of at least pH 5.5 following sugar challenge;

k. reduce plaque accumulation;

l. Treat, relieve or reduce dry mouth;

m. whiten teeth;

n. enhance systemic health, including cardiovascular health, o. reduce erosion of the teeth;

p. immunize the teeth against cariogenic bacteria and their effects, q. clean the teeth and oral cavity;

r. reduce inflammation; and s. increase anti-oxidant levels.

11. An oral care composition comprising:

precipitated calcium carbonate (PCC); and a preservative combination consisting essentially of pentylene glycol in an amount of about 0.1 wt % to 5.0 wt % and caprylyl glycol in an amount of about 0.1 wt % to 1.0 wt % wherein the composition achieves a log reduction in microbial bioburden of greater than 6 after 24 hours when challenged with bacterial pool assay in a surfactant-free PCC base.

* * * * *